US006278019B1

(12) United States Patent
Nakatani et al.

(10) Patent No.: US 6,278,019 B1
(45) Date of Patent: Aug. 21, 2001

(54) PROCESS FOR ACYLOXYLATING SIDE CHAINS OF ALKYL-SUBSTITUTED AROMATIC COMPOUNDS AND CATALYSTS USED THEREFOR

(75) Inventors: Jiro Nakatani; Eiichi Minomiya, both of Aichi; Tetsuya Kato, Kanagawa; Satoru Miyata, Aichi, all of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/284,815
(22) PCT Filed: Jun. 19, 1998
(86) PCT No.: PCT/JP98/02746
§ 371 Date: May 27, 1999
§ 102(e) Date: May 27, 1999
(87) PCT Pub. No.: WO99/11598
PCT Pub. Date: Mar. 11, 1999

(30) Foreign Application Priority Data

Aug. 29, 1997 (JP) .................................................. 9-234207
Dec. 11, 1997 (JP) .................................................. 9-341740

(51) Int. Cl.$^7$ .................................................. C07C 63/64
(52) U.S. Cl. .................................................. 562/495
(58) Field of Search .................................................. 562/495

(56) References Cited

U.S. PATENT DOCUMENTS 3,448,021 * 6/1969 Koehl .

* cited by examiner

Primary Examiner—Paul J. Killos
(74) Attorney, Agent, or Firm—Schnader Harrison Segal & Lewis LLP

(57) ABSTRACT

The present invention is a method for acyloxylating an alkyl group substituted aromatic compound at the side chain, by letting the alkyl group substituted aromatic compound and a carboxylic acid and/or a carboxylic anhydride react with each other in the presence of an oxygen containing gas. In this case, if (1) a solid catalyst in which at least one selected from cobalt, cerium and manganese is supported on a solid material or (2) a catalyst containing at least one selected from cobalt oxides, cerium oxides and manganese oxides is used, an alkali group substituted aromatic compound and a carboxylic acid and/or a carboxylic anhydride can be caused to react with each other efficiently in the presence of an oxygen containing gas, and in addition the catalyst can be easily separated from the reaction solution.

Furthermore, (3) a compound diacyloxylated at the side chains can be highly selectively produced if a cerium compound is used as a catalyst in the absence of a cobalt compound and a manganese compound.

Moreover, the present invention relates to a method for producing a cinnamic acid by letting a benzylidene diacetate react in the presence of a basic catalyst.

The alkyl group substituted aromatic compounds acyloxylated and diacyloxylated at the side chain obtained in the present invention are useful for perfumes, and the benzyl alcohols and benzaldehydes obtained by hydrolyzing them are useful for intermediate products of agricultural chemicals, drugs and perfumes and also for resin additives. The cinnamic acids produced according to the present invention are useful for intermediate products of agricultural chemicals, drugs and perfumes.

24 Claims, No Drawings

PROCESS FOR ACYLOXYLATING SIDE CHAINS OF ALKYL-SUBSTITUTED AROMATIC COMPOUNDS AND CATALYSTS USED THEREFOR

TECHNICAL FIELD

The present invention relates to (1) a Process for acyloxylating side chain of alkyl substituted aromatic compounds by causing the alkyl group substituted aromatic compound and a carboxylic acid and/or a carboxylic anhydride to react with each other in the presence of an oxygen containing gas, and catalysts used for said reaction, and (2) a method for producing a cinnamic acid by causing a benzylidene diacetate to react in the presence of a basic catalyst.

Alkyl group substituted aromatic compounds acyloxylated and diacyloxylated at the side chain (in the present invention, these compounds may be simply called compounds acyloxylated at the side chain) are useful for perfumes, and benzyl alcohols and benzaldehydes obtained by hydrolyzing them are useful for intermediate products of agricultural chemicals, pharmaceuticals and perfumes and also for resin additives. Cinnamic acids are useful for intermediate products of agricultural chemicals, pharmaceuticals and perfumes.

PRIOR ARTS

As methods for producing an alkyl group substituted aromatic compound acyloxylated or diacyloxylated at the side chain from the corresponding alkyl group substituted aromatic compound, (1) Japanese Patent Publication (Kokoku) No. 51-45572 discloses a method of using a cobalt compound as a catalyst in a liquid phase in the presence of acetic anhydride, and (2) Japanese Patent Laid-Open (Kokai) No. 56-10486 and Japanese Patent Laid-Open (Kokai) No. 56-57723 disclose a method of using a cobalt compound and/or a manganese compound as a catalyst and a halogen compound as a co-catalyst in a liquid phase in the presence of acetic anhydride.

As methods for synthesis of a cinnamic acid, (3) Journal of American Chemical Society, Vol. 79, P. 220 (1957), U.S. Pat. No. 3470151, etc. disclose the Perkin reaction that a benzaldehyde reacts with acetic anhydride in the presence of sodium acetate, and (4) Journal of American Chemical Society, Vol. 69, P. 852 (1947), U.S. Pat. No. 3470151, etc. discloses the Knoevenagel condensation reaction wherein benzoaldehydes react with malonic acid in the presence of organic base catalyst such as pyridine.

DISCLOSURE OF THE INVENTION

However, in the methods for producing an alkyl group substituted aromatic compound acyloxylated or diacyloxylated at the side chain from the corresponding alkyl group substituted aromatic compound, method (1) is very low in the rate of producing the compound diacyloxylated at the side chain and also low in selectivity. Method (2) is still insufficient in production rate and also low in the selectivity of the compound diacyloxylated at the side chain, though the rate of producing the compound diacyloxylated at the side chain is improved by using a halogen compound as a co-catalyst.

Furthermore, the ammonium ions in the ammonium bromide used as a co-catalyst are oxidized during reaction, to produce 2 moles of water from 1 mole of ammonium ions. As a result, the carboxylic anhydride existing in the reaction system quickly reacts with the produced water, to be converted into the carboxylic acid. That is, if ammonium ions exist in the reaction system, the decomposition of the carboxylic anhydride acting as an acetoxylating agent occurs significantly. Furthermore, also when crystal water is contained in the catalyst or co-catalyst, the decomposition of the carboxylic anhydride occurs significantly for the same reason.

Furthermore, since the catalysts used in said methods (1) and (2) are soluble in the reaction solution, it is difficult to recover them. Even if they can be recovered, a complicated recovery operation is necessary. So, these methods are not preferable as industrial methods for producing an alkyl group substituted aromatic compound diacyloxylated at the side chain from the corresponding alkyl group substituted aromatic compound.

Moreover, in the methods for synthesis of a cinnamic acid, said methods (3) and (4) are insufficient in the yield of the cinnamic acid, and to improve the yield, acetic anhydride or malonic acid must be used in an excessive amount for the substrate. In addition, said method (4) has a problem that expensive malonic acid must be used, and is not a preferable industrial method for producing a cinnamic acid. Furthermore, the benzaldehyde as a starting raw material is relatively unstable and if it is allowed to stand in air, it is gradually oxidized, to be converted into a benzoic acid. So, its handling is difficult.

An object of the present invention is to provide a method for acyloxylating an alkyl group substituted aromatic compound at the side chain, which is high in reaction efficiency, industrially applicable and high in productivity.

Another object of the present invention is to provide catalysts used for acyloxylating an alkyl group substituted aromatic compound at the side chain, which is high in reaction efficiency and can be easily separated from the reaction solution.

A further other object of the present invention is to provide a method for producing a cinnamic acid at a high yield, which is industrially applicable and high in productivity.

To solve the above problems, the inventors studied intensively, and as a result found that if (1) a solid catalyst in which at least one selected from cobalt, cerium and manganese is supported on a solid material or (2) a catalyst containing at least one selected from cobalt oxides, cerium oxides and manganese oxides is used, an alkyl group substituted aromatic compound and a carboxylic acid and/or a carboxylic anhydride can be caused to react with each other efficiently in the presence of an oxygen containing gas, and in addition, that the catalyst can be easily separated from the reaction solution. Furthermore, it was found that (3) a compound diacyloxylated at the side chain can be produced with high selectivity if a cerium compound is used as a catalyst in the absence of a cobalt compound and a manganese compound. Moreover, it was found that (4) if a halogen compound containing neither crystal water nor ammonium ion is used when a solid catalyst in which at least one selected from cobalt, cerium and manganese is supported on a solid material or a catalyst containing at least one selected from cobalt oxides, cerium oxides and manganese oxides is used as a catalyst, or when a cerium compound is used as a catalyst in the absence of a cobalt compound and a manganese compound, while said halogen compound is used as a co-catalyst, then an alkyl group substituted aromatic compound and a carboxylic anhydride can be caused to react with each other efficiently in the presence of an oxygen containing gas, and in addition that the decomposition of the carboxylic anhydride can be inhibited. It was also found that (5) if a halogen compound is supplied to the reaction system continuously or intermittently during reaction when a solid catalyst in which at least one selected from cobalt, cerium and manganese is supported on a solid material or a catalyst containing at least one selected from cobalt oxides, cerium oxides and manganese oxides is used as a catalyst, or when a cerium compound is used as a catalyst in the absence of a cobalt compound and a manganese compound, while said halogen compound is used as a co-catalyst, then an alkyl group substituted aromatic compound and a carboxylic acid and/or a carboxylic anhydride can be caused to react with each other efficiently in the presence of an oxygen containing gas. Thus, the present invention has been completed.

Furthermore, it was found that if a benzylidene diacetate is used as a raw material as a new method for producing a cinnamic acid, the corresponding cinnamic acid can be produced at a high yield, to complete the present invention.

That is, the present invention provides a method for acyloxylating an alkyl group substituted aromatic compound at the side chain, in which an alkyl group substituted aromatic compound and a carboxylic acid and/or a carboxylic anhydride are caused to react with each other in the presence of an oxygen containing gas, to produce an alkyl group substituted aromatic compound acyloxylated or diacyloxylated at the side chain, comprising the use of (1) a solid catalyst in which at least one selected from cobalt, cerium and manganese is supported on a solid material or (2) a catalyst containing at least one selected from cobalt oxides, cerium oxides and manganese oxides or (3) a cerium compound catalyst in the absence of a cobalt compound and a manganese compound. The present invention also provides catalysts used for said method. Furthermore, the present invention provides a method for acyloxylating an alkyl group substituted aromatic compound at the side chain, comprising the step of using a halogen compound containing neither crystal water nor ammonium ion and/or supplying a halogen compound into the reaction system continuously or intermittently during reaction, when a solid catalyst in which at least one selected from cobalt, cerium and manganese is supported on a solid material or a catalyst containing at least one selected from cobalt oxides, cerium oxides and manganese oxides is used as a catalyst, or when a cerium compound is used as a catalyst in the absence of a cobalt compound and a manganese compound, while said halogen compound is used as a co-catalyst. The present invention also provides catalysts used for said method.

The present invention also provides a method for producing a cinnamic acid, comprising the step of heating a benzylidene diacetate in the presence of a basic catalyst, for reaction.

THE BEST EMBODIMENTS OF THE INVENTION (Method for producing a compound acyloxylated at the side chain)

In the present invention, the supports on at least one selected from cobalt, cerium and manganese is not especially limited, but in view of thermal stability and solvent resistance, an inorganic compound can be preferably used. The supports which can be used here include, for example, zeolite, alumina, silica-alumina, silica, titania, activated clay, active carbon, etc. In the present invention, especially zeolite, alumina, silica-alumina and active carbon are preferable.

As for the structure of the alumina used in the present invention, among $\alpha$, $\kappa$, $\theta$, $\delta$, $\gamma$, $\eta$, $\chi$ and $\rho$ types, others than $\alpha$ type can be preferably used, and a mixture thereof can also be used. Alumina is generally marketed, and such marketed products can also be used.

The silica-alumina used in the present invention is amorphous, and the alumina content is not especially limited. Silica-alumina is also generally marketed, and such marketed products can also be used. The active carbon used in the present invention is not especially limited, and marketed active carbon can also be used.

The zeolites used in the present invention can be of any structure, and preferable are MFI type, beta type, faujasite type and mordenite type. The zeolite used in the present invention can be either experimentally synthesized zeolite or marketed zeolite. The methods for synthesis of MFI type zeolite are disclosed, for example, in U.S. Pat. Nos. 3,702,886 and 4,511,547. A method for synthesis of beta type zeolite is disclosed, for example, in U.S. Pat. No. 3,308,069. A method for synthesis of mordenite type zeolite is disclosed, for example, in Japanese Patent Publication F (Kokoku) No. 47-46677. Methods for synthesis of faujasite type zeolite are disclosed, for example, in Japanese Patent Publication (Kokoku) No. 38-5806, etc.

In the present invention, the method for introducing at least one selected from cobalt, cerium and manganese onto a support is not especially limited. The introduction methods include ion exchange, impregnation and a method of adding at least one selected from cobalt, cerium and manganese to a synthetic gel precursor of a support, followed by hydrothermal treatment or calcination for letting any of these metals be contained in the support.

In the case of ion exchange, a method of dispersing a support into a solution containing at least one selected from cobalt, cerium and manganese and in some cases, adding an alkaline solution such as ammonia water into the dispersion for pH adjustment can also be preferably used. Furthermore, With repeating this operation if necessary, the desired amount of at least one selected from cobalt, carium and manganese can be introduced. The compound used as at least one selected from cobalt, cerium and manganese can be an organic salt such as formate, acetate, propionate, butyrate, valerate, caproate or naphthenate, or an inorganic salt such as chloride, bromide, iodide, oxide, hydroxide, carbonate, sulfate, nitrate or perchlorate.

In the present invention, it is preferable that the amount of at least one selected from cobalt, cerium and manganese contained in the support is 0.1 to 30 wt % based on the weight of the support. A more preferable range is 1 to 10 wt %.

In the present invention, if zeolite is used as the support, it is preferable that the zeolite further contains hydrogen ions. Hydrogen ions can be introduced into zeolite by direct ion exchange with an acid aqueous solution, or by exchanging with ammonium ions followed by calcination. If the ions at cation sites are organic cations containing nitrogen atom, they can be decomposed by calcination for conversion into hydrogen ions.

The cobalt oxides in the present invention refer to compounds in which a cobalt atom is combined with at least one oxygen atom, and include, for example, cobaltous oxide (CoO), tricobalt tetroxide ($Co_3O_4$) and cobaltic oxide ($Co_2O_3$), and also mixtures thereof.

The cerium oxides refer to compounds in which a cerium atom is combined with at least one oxygen atom, and include, for example, cerous oxide ($Ce_2O_3$) and ceric oxide ($CeO_2$) and a mixture thereof.

The manganese oxides refer to compounds in which a manganese atom is combined with at least one oxygen atom, and include, for example, manganous oxide (MnO), trimanganese tetroxide ($Mn_3O_4$), manganic oxide ($Mn_2O_3$), manganese dioxide ($MnO_2$) and dimanganese heptoxide ($Mn_2O_7$) and mixtures thereof.

The raw compounds for producing the cobalt oxides, cerium oxides and manganese oxides used in the present invention are not especially limited, and include, for example, sulfates, nitrates, formates, acetates, propionates, phosphates, oxalates, carbonates, hydroxides, oxides, bromides, chlorides, naphthenates, benzoates, stearates, acetylacetonates, etc. If these are calcined at higher than 300° C. without or after hydrolysis with alkali water, etc., the intended oxides can be obtained. Marketed oxides can also be used without further treatment.

When a catalyst of the present invention is used for reaction, a catalyst containing only one selected from cobalt oxides, cerium oxides and manganese oxides can be used or two or more of them can also be used in combination. The methods for preparing a catalyst consisting of two or more oxides include (1) a physical mixing preparation method of finely grinding respective oxides while sufficiently mixing them, and (2) a chemical preparation method of sufficiently mixing raw compounds of oxides, followed by calcination, the mixture or dissolving the mixture into a solvent, coprecipitating by alkali water, etc. followed by calcination. In the present invention, a chemical preparation can be preferably used since different metals can be mixed with the atom level.

In the present invention, a solid catalyst in which at least one selected from cobalt, cerium and manganese is supported on a solid material or a catalyst containing at least one of cobalt oxides, cerium oxides and manganese oxides can be used as it is or after it has been formed. The forming method is not especially limited, and any known method such as extrusion or compression can be used, and the catalyst can be formed into spheres, columns, honeycombs or any other proper form. If necessary, an inorganic oxide such as silica, alumina or magnesia or clay can also be used as a binder for forming.

The reaction using a solid catalyst in which at least one selected from cobalt, cerium and manganese is supported on a solid material or a catalyst containing at least one selected from cobalt oxides, cerium oxides and manganese oxides can be effected by any desired method such as fixed bed method, fluidized bed method or suspended catalyst method.

The amount of the catalyst used depends on the reaction method and reaction conditions. In the case of batch operation or semi-batch operation, etc., the amount is 0.1 to 100 wt % based on the total amount of the alkyl group substituted aromatic compound. A preferable range is 1 to 50 wt %. In the case of continuous operation or intermittent operation, the ratio of the hourly supplied weight of the alkyl group substituted aromatic compound per weight of the catalyst is 0.1 to 30 $h^{-1}$. A preferable range is 0.5 to 5 $h^{-1}$.

The cerium compound used in the present invention is not especially limited. The cerium compounds which can be used here include sulfate, nitrate, formate, acetate, propionate, phosphate, oxalate, carbonate, hydroxide, oxide, bromide, chloride, naphthenate, benzoate, stearate, acetylactonate, etc., andacerium compound is properly selected in combination with the alkyl group substituted aromatic compound used as the reaction substrate and an acyloxylating agent. If a cerium compound soluble in the reaction system is used, the yield of the alkyl group substituted aromatic compound diacyloxylated at the side chain can be further improved. If the cerium compound is slightly soluble in the reaction solution, a proper solvent can be added to it for dissolving it. Specific cerium compounds which can be used here include cerium nitrate, cerium sulfate, cerium tetrammonium sulfate, cerium acetate, cerium hydroxide, cerium oxide, cerium oxalate, cerium carbonate, cerium chloride, cerium fluoride, cerium acetylacetonate, cerium bromide, etc.

It is preferable that the amount of the cerium compound used is 0.0001 to 0.5 molar time based on the amount of the alkyl group substituted aromatic compound. A more preferable range is 0.001 to 0.1 molar time.

The alkyl group substituted aromatic compound used in the present invention refers to an aromatic compound substituted by one alkyl group, or an aromatic compound in which at least one substituent group selected from alkyl group, allyl group, aryl group, halogen group, nitro group, cyano group, amino group, amide group, alkoxyl group, acyl group, carboxyl group, formyl group, acyloxy group, hydroxyl group and hydroxymethyl group is additionally directly combined with an aromatic ring.

Specific alkyl group substituted aromatic compounds which can be used here include toluene, ethylbenzene, o-xylene, m-xylene, p-xylene, diethylbenzene, o-chlorotoluene, m-chlorotoluene, p-chlorotoluene, dichlorotoluene, o-nitrotoluene, m-nitrotoluene, p-nitrotoluene, o-methoxytoluene, m-methoxytoluene, p-methoxytoluene, o-phenoxytoluene, m-phenoxytoluene, p-phenoxytoluene, o-cyanotoluene, m-cyanotoluene, p-cyanotoluene, o-toluic acid, m-toluic acid, p-toluic acid, o-tolualdehyde, m-tolualdehyde, p-tolualdehyde, o-cresol, m-cresol, p-cresol, o-methylbenzyl alcohol, m-methylbenzyl alcohol, p-methylbenzyl alcohol, etc.

The carboxylic acid used in the present invention can be either an aromatic carboxylic acid or aliphatic carboxylic acid. An aliphatic carboxylic acid is preferable. The carboxylic anhydride can be either an aromatic carboxylic anhydride or aliphatic carboxylic anhydride. An aliphatic carboxylic anhydride is preferable.

Specific carboxylic acids which can be used here include formic acid, acetic acid, acetic anhydride, chloroacetic acid, chloroacetic anhydride, dichloroacetic acid, dichloroacetic anhydride, trichloroacetic acid, trichloroacetic anhydride, propionic acid, propionic anhydride, chloropropionic acid, dichloropropionic acid, trichloropropionic acid, n-butyric acid, n-butyric anhydride, iso-butyric acid, iso-butyric anhydride, valeric acid, valeric anhydride, maleic acid, maleic anhydride, succinic acid, succinic anhydride, phthalic acid, phthalic anhydride, benzoic acid, benzoic anhydride, etc.

The amount of the carboxylic acid and/or carboxylic anhydride used (the total amount) is 0.1 to 50 molar times based on the amount of the alkyl group substituted aromatic compound used as the raw material. A preferable range is 1 to 10 molar times. If the amount is too small, the effect of the present invention declines. If too large, it is costly to recover the unreactive carboxylic acid and/or carboxylic anhydride, which is industrially disadvantageous.

In the present invention, it is preferable to let a halogen compound exist in the reaction system as a co-catalyst. At least either of a chloride compound or bromine compound is suitable. A bromine compound is preferable. More preferable is a bromine compound containing neither crystal water nor ammonium ion. If a halogen compound containing neither crystal water nor ammonium ion is used, the decomposition of the carboxylic anhydride used as an acetoxylating agent can be inhibited when the alkyl group substituted aromatic compound and the carboxylic anhydride are caused to react with each other in the presence of an oxygen containing gas. If a halogen compound containing crystal water is used after dehydration treatment, a similar effect can be obtained.

The chlorine compounds which can be used here include organic chlorine compounds such as alkyl chlorides and organic acid chlorides, hydrochlorides of alkali metals and alkaline earth metals, ammonium salts, etc. Specific chlorine compounds include chlorine, lithium chloride, sodium chloride, potassium chloride, cesium chloride, magnesium chloride, calcium chloride, strontium chloride, barium chloride, manganese chloride, cobalt chloride, zinc chloride, aluminum chloride, hydrogen chloride, ammonium chloride, benzyl chloride, benzal chloride, benzoyl chloride, dichloroethane, tetrachloroethane, acetyl chloride, etc.

The bromine compounds which can be used here include organic bromine compounds such as alkyl bromides and organic acid bromides, bromides of alkali metals, alkaline earth metals and transition metals, ammonium salts, etc.

Specific bromine compounds include bromine, lithium bromide, sodium bromide, potassium bromide, cesium bromide, magnesium bromide, calcium bromide, strontium bromide, barium bromide, manganese bromide, cobalt bromide, zinc bromide, aluminum bromide, hydrogen bromide, ammonium bromide, benzyl bromide, benzal bromide, benzoyl bromide, dibromoethane, tetrabromoethane, acetyl bromide, etc.

As for the method of adding a halogen compound, all the amount can be added to the reaction system before the start of reaction. However, if it is added continuously or intermittently at a proper rate during reaction, the alkyl group substituted aromatic compound conversion rate is improved more preferably.

For continuously and intermittently supplying a halogen compound, a solid halogen compound can be supplied continuously or intermittently. However, a halogen compound can be dissolved in a proper solvent, for supplying as a solution, or if vapor pressure of bromine, etc. is available, it can be supplied into the reaction system using a carrier gas. A part of a halogen compound can also be added to the reaction system before start of reaction as practiced in the conventional methods.

It is preferable that the amount of the halogen compound used is 0.0001 to 0.5 molar based on the amount of the alkyl group substituted aromatic compound used as the raw material. A more preferable range is 0.001 to 0.1 molar.

In the present invention, it is preferable to let a zinc compound exist further in the reaction system as a co-catalyst.

The zinc compound used in the present invention is not especially limited. The zinc compounds which can be used here include sulfate, nitrate, formate, acetate, propionate, phosphate, oxalate, carbonate, hydroxide, oxide, bromide, chloride, naphthenate, benzoate, stearate, acetylacetonate, etc.

It is preferable that the amount of the zinc compound used is 0.0001 to 0.5 molar based on the amount of the alkyl group substituted aromatic compound used as the raw material. A more preferable range is 0.001 to 0.1 molar.

The oxygen containing gas used in the present invention is not required to be pure oxygen, and can be oxygen diluted by an inert gas, etc., for example, air. The necessary amount of oxygen is theoretically 0.5 mole per 1 mole of the alkyl group substituted aromatic compound. It is allowed that the oxygen is caused to exist by more than the theoretical amount for enhancing the reaction rate and that the system is pressurized to raise the solubility of oxygen in the reaction solution.

It is preferable that the reaction of the present invention is effected in a liquid phase. The reaction temperature is usually 20 to 500° C., preferably 60 to 350° C. The reaction pressure is not especially limited, but is set to keep the reaction system in a liquid phase. These reaction conditions are properly selected in reference to the combination of the alkyl group substituted aromatic compound and the carboxylic acid or carboxylic anhydride caused to react with each other, needless to say.

After completion of reaction, the alkyl group substituted aromatic compound acyloxylated or diacyloxylated at the side chains produced from the reaction solution can be isolated and purified by ordinary distillation, crystallization or chromatography, etc. Before isolation and purification, the compound acyloxylated or diacyloxylated at the side chains can also be hydrolyzed, to get the aromatic alcohol or aromatic aldehyde. If unreactive raw materials are recovered, they can be used again for acyloxylation reaction.

As described above, the present invention is very advantageous as a method for industrially producing an alkyl group substituted aromatic compound diacyloxylated at the side chains, since the alkyl group substituted aromatic compound can be efficiently acyloxylated at the side chains.

(Method for producing a cinnamic acid)

The basic catalyst in the present invention can be either an organic base compound or inorganic base compound. That a compound is basic can be easily confirmed by dipping pH test paper, measuring its aqueous solution using a pH meter, observing the discoloration caused by an indicator or measuring the adsorption of carbonic acid gas, etc. The organic base compounds which can be used here include organic amines such as pyridine, pyrrolidine, methylamine, dimethylamine, trimethylamine, ethylamine, diethylamine, triethylamine, tetraethylammonium hydroxide, tetramethylammonium hydroxide, aniline and toluidine. The inorganic base compounds which can be used here are salts of strong bases and weak acids, and include, for example, alkali metal acetates, alkali metal propionates, alkali metal carbonates, alkaline earth metal acetates, alkaline earth metal propionates, alkaline earth metal carbonates, etc.

The amount of the basic catalyst used depends on the reaction substrate and reaction conditions. It is preferable that the amount is 0.01 to 5 molar times based on the amount of the benzylidene diacetate. A more preferable range is 0.2 to 1 molar time.

The benzylidene diacetate used in the present invention is not especially limited, and can be, for example, a benzylidene diacetate represented by the following general formula (1):

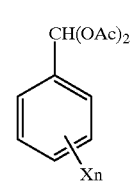

(1)

(where X stands for at least one selected from hydrogen atom, halogen group, alkoxy group, hydroxyl group, acyloxy group, nitro group, allyl group, alkyl group, aryl group, cyano group, amino group, amide group, acyl group, carboxyl group, formyl group and hydroxymethyl group, and n stands for 1 to 5.) It is preferable that the alkoxy group, alkyl group and amide group respectively have 1 to 6 carbon atoms, that the acyloxy group, allyl group and acyl group respectively have 2 to 6 carbon atoms, and that the aryl group has 6 to 12 carbon atoms. More preferable benzylidene diacetates include benzylidene diacetate, chlorobenzylidene diacetate, dichlorobenzylidene diacetate, nitrobenzylidene diacetate, methoxybenzylidene diacetate, hydroxybenzylidene diacetate, acetoxybenzylidene diacetate, phenoxybenzylidene diacetate, etc.

The benzylidene diacetate used in the present invention can be pure benzylidene diacetate or a composition containing it. For example, the reaction solution containing the benzylidene diacetate produced by acetoxylating a methyl group substituted aromatic compound in acetic acid and/or acetic anhydride can also be used as a reaction raw material of the present invention.

When the benzylidene diacetate obtained by acetoxylating a methyl group substituted aromatic compound in acetic anhydride is caused to react in the presence of a basic catalyst, the methyl group substituted aromatic compound used in the present invention is not especially limited, but can be, for example, a compound represented by the following general formula (2):

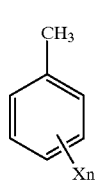

(2)

(where X stands for at least one selected from hydrogen atom, halogen group, alkoxy group, hydroxyl group, acyloxy group, nitro group, allyl group, alkyl group, aryl group, cyano group, amino group, amide group, acyl group, carboxyl group, formyl group and hydroxymethyl group, and n stands for 1 to 5.)

It is preferable that the alkoxy group, alkyl group and amide group respectively have 1 to 6 carbon atoms, that the acyloxy group, allyl group and acyl group respectively have 2 to 6 carbon atoms, and that the aryl group has 6 to 12 carbon atoms. More preferable methyl group substituted aromatic compounds include toluene, xylene, chlorotoluene, dichlorotoluene, nitrotoluene, methoxytoluene, phenoxytoluene, cresol and methylbenzyl alcohol.

The reaction of the present invention can be effected using only a benzylidene diacetate and a basic catalyst, but acetic anhydride can also coexist in the reaction system. Acetic anhydride has an effect to promote the reaction and enhances the yield of the cinnamic acid. The coexisting amount of acetic anhydride depends on the reaction substrate and reaction conditions. It is preferable that the amount is 0.01 to 10 molar times based on the amount of the benzylidene diacetate. A more preferable range is 0.1 to 5 molar times. If the coexisting amount of acetic anhydride is too small, the effect is small, and if too large on the contrary, the unreactive acetic anhydride must be recovered economically less advantageously though the intended effect can be achieved.

In the present invention, any proper solvent can also be used. The proper solvents which can be used here are those which are inactive to the benzylidene diacetate and the organic alkali salt used under the reaction conditions, and include, for example, acetic acid, hexane, cyclohexane, petroleum ether, diethyl ether, tetrahydrofuran, nitrobenzene, chlorobenzene, dichlorobenzene, trichlorobenzene, etc. It is preferable that the amount of the solvent used is usually 1 to 10 times based on the total amount of the benzylidene diacetate used for reaction.

The reaction temperature in the present invention can be properly selected, depending on the reaction substrate and reaction conditions. A preferable range is 100 to 300° C. A more preferable range is 120 to 250° C. In the case of batch operation or semi-batch operation, etc., the reaction time is usually 0.5 to 24 hours. A preferable range is 1 to 12 hours. The reaction pressure is not especially limited, and either atmospheric pressure or pressurization can be adopted, depending on the reaction substrate, etc.

After completion of the reaction, the produced cinnamic acid can be isolated from the reaction system by extracting with an alkaline aqueous solution, and adding an acid to the aqueous extract for making the extract neutral or acid. Furthermore, if the unreactive raw materials are recovered, they can also be used for reaction again.

As described above, the present invention is very advantageous as a new method for industrially producing a cinnamic acid, since the cinnamic acid can be obtained at a high yield by heating a benzylidene diacetate in the presence of a basic catalyst, for reaction.

EXAMPLES

The present invention is described below in reference to examples, but is not limited thereto or thereby. In the following examples, MFI type zeolite used was synthesized by the method stated in Japanese Patent Publication (Kokoku) No. 60-35284 ($SiO_2/Al_2O_3$ molar ratio=25, Na ion type), and the beta type zeolite used was CP811BL-25 produced by PQ Corporation ($SiO_2/Al_2O_3$ molar ratio=25, hydrogen ion type). The Y type zeolite used was 320NAA produced by Tosoh Corp. ($SiO_2/Al_2O_3$ molar ratio=5.1, Na ion type). The alumina used was activated alumina produced by Nikka Seiko. The silica alumina used was N633L produced by Nikki Kagaku (alumina content 13 wt %). The active carbon used was active carbon powder special grade produced by Wako Junyaku Kogyo.

The cobalt compound used for preparing the catalyst was cobalt (II) acetate tetrahydrate produced by Nacalai Tesque. The manganese compound used was special grade manganese (II) acetate tetrahydrate produced by Katayama Kagaku. The palladium compound used was special grade palladium (II) chloride produced by Nacalai Tesque. The copper compounds used were special grade copper (II) acetate monohydrate and copper (II) oxide produced by Wako Junyaku. The vanadium compound used was vanadium (V) pentoxide produced by Katayama Kagaku. The ammonium salt used was first grade ammonium chloride produced by Kanto Kagaku. The halides used were ammonium bromide and magnesium bromide hexahydrate ($MgBr_2.6H_2O$) produced by Katayama Kagaku, magnesium bromide ($MgBr_2$)produced by ALDRICH, and zinc bromide ($ZnBr_2$) and bromine produced by Wako Junyaku. The cerium compound used was special grade cerous (III) acetate monohydrate produced by Nacalai Tesque. The zinc compound used was first grade zinc (II) acetate produced by Katayama Kagaku.

The alkyl group substituted aromatic compounds used in the following examples were special grade m-phenoxytoluene produced by Wako Junyaku and special grade m-chlorotoluene and m-cyanotoluene produced by Tokyo Kasei. The acyloxylating agent used was first grade acetic anhydride produced by Kanto Kagaku.

The basic catalysts used in the following examples were first grade sodium acetate and potassium acetate produced by Katayama Kagaku. The raw materials for synthesizing benzylidene diacetates were m-chlorobenzaldehyde produced by Wako Junyaku and first grade acetic anhydride produced by Kanto kagaku.

Preparation of Catalysts

Catalyst 1

Twenty grams of Na ion type zeolite with MFI structure was dispersed into 40 ml of 10% ammonium chloride aqueous solution, and the mixture was stirred at 80° C. for 2 hours, and filtered. The residue was washed by 250 ml of distilled water twice. This ion exchange operation was further repeated 4 times. Then, the residue was dispersed into 250 ml of an aqueous solution containing 7.6 g of cobalt (II) acetate tetrahydrate, and the mixture was stirred at 80° C. for 2 hours and filtered. The residue was washed by 250 ml of distilled water twice. This operation was further repeated twice. The residue was dried at 110° C. overnight, and calcined in an electric furnace at 500° C. for 2 hours, to prepare MFI type zeolite containing cobalt ions and hydrogen ions (Co+H–MFI).

Catalyst 2

Twenty grams of hydrogen ion type zeolite with beta structure was dispersed into 250 ml of an aqueous solution containing 10 g of cobalt (II) acetate tetrahydrate, and the mixture was stirred at 80° C. for 2 hours and filtered. The residue was washed by 250 ml of distilled water twice. This operation was further repeated twice. The residue was dried overnight at 110° C. and calcined in an electric furnace at 500° C. for 2 hours, to prepare a beta type zeolite containing cobalt ions and hydrogen ions (Co+H–β).

Catalyst 3

A Y type zeolite containing cobalt ions and hydrogen ions (Co+H–Y) was prepared as described for preparing the catalyst 1, except that 20 g of Na ion type Y type zeolite was used and that 18.6 g of cobalt (II) acetate tetrahydrate was used for cobalt ion exchange.

Catalyst 4

An MFI type zeolite containing manganese ions and hydrogen ions (Mn+H–MFI) was prepared as described for preparing the catalyst 1, except that 20 g of Na ion type MFI type zeolite was used and that 7.4 g of manganese (II) acetate tetrahydrate was used instead of 7.6 g of cobalt (II) acetate tetrahydrate.

Catalyst 5

Twenty grams of silica-alumina was immersed in 40 ml of an aqueous solution with 2.39 g of cerium acetate monohydrate dissolved, and the mixture was evaporated to dryness. The residue was calcined at 500° C. for 1 hour (Ce/SiO$_2$—Al$_2$O$_3$).

Catalyst 6

Ten grams of silica-alumina was immersed in 20 ml of an aqueous solution with 0.64 g of cobalt (II) acetate tetrahydrate, 0.514 g of cerous acetate monohydrate and 1.46 of zinc (II) acetate dihydrate dissolved, and the mixture was evaporated to dryness. The residue was calcined at 500° C. for 1 hour (Co+Ce+Zn/SiO$_2$—Al$_2$O$_3$).

Catalyst 7

A catalyst was prepared as described for preparing the catalyst 6, except that 10 g of alumina was used (Co+Ce+Zn/Al$_2$O$_3$).

Catalyst 8

Fifteen grams of active carbon was immersed in 20 ml of an aqueous solution with 0.96 g of cobalt (II) acetate tetrahydrate, 0.76 g of cerous acetate monohydrate and 2.23 g of zinc (II) acetate dihydrate dissolved, and the mixture was evaporated to dryness. The residue was burned at 500° C. for 1 (Co+Ce+Zn/C).

Catalyst 9

An MFI type zeolite containing copper ions and hydrogen ions (Cu+H–MFI) was prepared as described for preparing the catalyst 1, except that 20 g of Na ion type MFI type zeolite was used and that 6.9 g of copper (II) acetate dihydrate was used instead of 7.6 g of cobalt (II) acetate tetrahydrate.

Catalyst 10

Twenty grams of Na ion type MFI type zeolite was dispersed in 40 ml of 10% ammonium chloride aqueous solution, and the mixture was stirred at 80° C. for 2 hours and filtered. The residue was washed by 250 ml of distilled water twice. This ion exchange operation was further repeated 4 times. The residue was dispersed in a solution with 2.0 g of palladium chloride dissolved in 250 ml 0.5M hydrochloric acid aqueous solution, and the mixture was stirred for 1 hour. Then, 30% ammonia water was added dropwise to achieve a pH of 8.0, and the mixture was stirred overnight at room temperature, and filtered. The residue was washed by 250 ml of distilled water twice. This operation was further repeated twice. It was dried overnight at 110° C., and calcined in an electric furnace at 500° C. for 2 hours, to prepare an MFI type zeolite containing palladium ions and hydrogen ions (Pd+H–MFI).

Evaluation of Catalysts

EXAMPLES 1 TO 4

A glass three-neck flask was charged with 107.3 g of acetic anhydride, a predetermined amount of a solid catalyst (any of said catalysts 1 to 4), 0.67 g of ceous (III) acetate as a co-catalyst, 0.88 g of zinc (II) acetate dihydrate and 0.78 g of ammonium bromide, and the mixture was stirred at 500 rpm using stirring blades, while air was bubbled in at 50 ml/min at atmospheric pressure. In succession, the three-neck flask was heated in an oil bath, to be kept at 90° C., and 23.4 g of m-phenoxytoluene was added at a time from a dropping funnel, to start reaction. After completion of reaction for a predetermined time, the reaction solution was separated from the solid catalyst, and the reaction solution was separated from the solid catalyst, and the reaction solution was analyzed by high performance liquid chromatography. The m-phenoxytoluene conversion, m-phenoxybenzyl acetate selectivity and m-phenoxybenzylidene diacetate selectivity were calculated respectively from the following formulae:

m-phenoxytoluene conversion (%)=(Moles of reacted m-phenoxytoluene)/(Moles of m-phenoxytoluene in the raw materials)×100 m-phenoxybenzyl acetate selectivity (%)=(Moles of produced m-phenoxybenzyl acetate)/(Moles of reacted m-phenoxytoluene)×100 m-phenoxybenzylidene acetate selectivity (%)=(Moles of produced m-phenoxybenzylidene diacetate)/(Moles of reacted m-phenoxytoluene)×100

The reaction conditions and results are shown in Tables 1 and 2.

EXAMPLES 5 to 8

A glass three-neck flask was charged with 107.3 g of acetic anhydride, a predetermined amount of a solid catalyst (any of said catalysts 5 to 8) and 0.78 g of ammonium bromide as a co-catalyst, and the mixture was stirred at 500 rpm using stirring blades, while air was bubbled in at 50 ml/min at atmospheric pressure. In succession, the three-neck flask was heated in an oil bath, to be kept at 90° C., and 23.4 g of m-phenoxytoluene was added at a time from a dropping funnel, to start reaction. After completion of reaction for a predetermined time, the reaction solution was separated from the solid catalyst, and the reaction solution was analyzed by high performance liquid chromatography. The reaction conditions and results are shown in Tables 1 and 2.

Comparative Examples 1 and 2

Operation was effected as described for Example 1, except that said catalyst 9 or 10 was used as the solid catalyst. The reaction conditions and results are shown in Tables 1 and 2.

EXAMPLE 9

Operation was effected as described for Example 5, except that said catalyst 8 was used and that 16.08 g of m-chlorotoluene was used instead of 23.4 g of m-phenoxytoluene. The m-chlorotoluene conversion, m-chlorobenzyl acetate selectivity and m-chlorobenzylidene diacetate selectivity were respectively calculated from the following formulae:

m-chlorotoluene conversion (%)=(Moles of reacted m-chlorotoluene)/(Moles of m-chlorotoluene in the raw materials)×100 m-chlorobenzyl acetate selectivity (%)=(Moles of produced m-chlorobenzyl acetate)/(Moles of reacted m-chlorotoluene)×100 m-chlorobenzylidene diacetate selectivity (%)=(Moles of produced m-chlorobenzylidene diacetate)/(Moles of reaction m-chlorotoluene)×100

The reaction results are shown in Table 3.

Comparative Example 3

Operation was effected as described for Example 9, except that said catalyst 9 was used as the solid catalyst. The reaction results are shown in Table 3.

TABLE 1

| | Reaction substrate *1 | Catalyst | Weight of catalyst (g) | Co-catalyst (g) | | |
|---|---|---|---|---|---|---|
| | | | | $Ce(CH_3COO)_3$—$H_2O$ | $Ze(CH_3COO)_3$—$2H_2O$ | $NH_4Br$ |
| Example 1 | MPT | Co + H-MFI | 4.77 | 0.67 | 0.88 | 0.78 |
| Example 2 | MPT | Co + H-β | 4.77 | 0.67 | 0.88 | 0.78 |
| Example 3 | MPT | Co + H-Y | 4.77 | 0.67 | 0.88 | 0.78 |
| Example 4 | MPT | Mn + H-MfI | 4.77 | 0.67 | 0.88 | 0.78 |
| Example 5 | MPT | Ce/$Sio_2$—$Al_2O_3$ | 5.60 | — | — | 0.78 |
| Example 6 | MPT | Co + Ce + Zn/$SiO_2$—$Al_2O_3$ | 4.77 | — | — | 0.78 |
| Example 7 | MPT | Co + Ce + Zn/$Al_2O_3$ | 4.77 | — | — | 0.78 |
| Example 8 | MPT | Co + Ce + Zn/C | 4.77 | — | — | 0.78 |
| Example 9 | MCT | Co + Ce + Zn/C | 1.0 | — | — | 0.78 |
| Comparative Example 1 | MPT | Cu + H-MFI | 4.77 | 0.67 | 0.88 | 0.78 |
| Comparative Example 2 | MPT | Pd + H-MFI | 4.77 | 0.67 | 0.88 | 0.78 |
| Comparative Example 3 | MCT | Cu + H-MFI | 4.77 | 0.67 | 0.88 | 0.78 |

*1: MPT = m-phenoxytoluene, MCT = m-chlorotoluene

TABLE 2

| | | | Reaction results *1 | | |
|---|---|---|---|---|---|
| | Reaction temperature (° C.) | Reaction time (h) | MPT conversion (%) | MPBACE selectivity (%) | MPBDACE selectivity (%) |
| Example 1 | 90 | 6 | 42.8 | 12.2 | 83.9 |
| Example 2 | 90 | 6 | 43.1 | 17.7 | 80.2 |
| Example 3 | 90 | 6 | 31.4 | 13.8 | 81.5 |
| Example 4 | 110 | 3 | 7.6 | 18.4 | 55.6 |
| Example 5 | 90 | 6 | 7.3 | 32.1 | 71.1 |
| Example 6 | 90 | 6 | 11.0 | 44.0 | 37.5 |
| Example 7 | 90 | 6 | 5.8 | 42.8 | 48.4 |
| Example 8 | 90 | 6 | 17.3 | 31.7 | 58.3 |
| Comparative Example 1 | 90 | 6 | 2.6 | 7.7 | 10.0 |
| Comparative Example 2 | 90 | 6 | 0.8 | 0 | 0 |

*1: MPT = m-phenoxytoluene, MPBACE = m-phenoxybenzyl acetate, MPBDACE = m-phenoxybenzylidene diacetate

TABLE 3

| | Reaction temperature (° C.) | Reaction time (h) | MPT conversion (%) | Reaction results *1 | |
| --- | --- | --- | --- | --- | --- |
| | | | | MPBACE selectivity (%) | MPBDACE selectivity (%) |
| Example 9 | 90 | 6 | 23.1 | 21.6 | 73.9 |
| Comparative Example 3 | 120 | 6 | 2.7 | 30.4 | 5.2 |

*1: MCT = m-chlorotoluene, MCBACE = m-chlorobenzyl acetate, MCBDACE = m-chlorobenzylidene diacetate From the above results, it can be seen that if a solid catalyst in which at least one selected from cobalt, cerium and manganese is supported on a solid material is used for producing an alkyl group substituted aromatic compound diacyloxylated at the side chains, the diacyloxylation reaction can take place efficiently. (Preparation of catalysts)

Catalyst 11

2.88 g of cobalt (II) acetate tetrahydrate, 2.28 g of cerous (III) acetate monohydrate and 6.69 g of zinc (II) acetate dihyrate were dissolved into 30 ml of 80° C. water, and the water was removed by evaporation to dryness. The residue was heated in air from room temperature at 3° C./min up to 350° C. and then at 5° C./min up to 500° C., being kept at the temperature for 2 hours, to prepare a compound oxide of cobalt, cerium and zinc.

Catalyst 12

2.88 g of cobalt (II) acetate tetrahydrate and 2.28 g of cerous (III) acetate monohydrate were dissolved into 30 ml of 80° C. water, and the water was removed by evaporation to dryness. The residue was heated in air from room temperature at 3° C./min up to 350° C. and then at 5° C./min up to 500° C., being kept at the temperature for 2 hours, to prepare a compound oxide of cobalt and cerium, Catalyst 13

2.88 g of cobalt (II) acetate tetrahydrate, 1.66 g of manganese (III) acetate tetrahydrate and 6.69 g of zinc (II) acetate dihyrate were dissolved into 30 ml of 80° C. water, and water was removed by evaporation to dryness. The residue was heated in air from temperature at 3° C./min up to 350° C. and then at 5° C./min up to 500° C., being kept at the temperature for 2 hours, to prepare a compound oxide of cobalt, cerium and zinc.

Catalyst 14

2.88 g of cerous (III)acetate monohydrate, 1.66 g of manganese (II) acetete tetrahydrate and 6.69 g of zinc (II) acetate dihyrate were dissolved into 30 ml of 80° C. water, and water was removed by evaporation to dryness. The residue was heated in air from room temperature at 3° C./min up to 350° C. and then at 5° C./min up to 500° C., being kept at the temperature for 2 hour, to prepare a compound oxide of cerium, manganese and zinc.

Catalyst 15

Special grade cerium (IV) oxide produced by Wako Junyaku was used as catalyst 15.

Catalyst 16

Copper (II) oxide produced by Wako Junyaku was used as catalyst 16.

Catalyst 17

6.69 g of zinc (II) acetate dihyrate was dissolved into 30 ml of 80° C. water, and 0.91 g of vanadium (V) pentoxide was added. The mixture was stirred, and water was removed by evaporation to dryness. The residue was heated in air from room temperature at 3° C./min up to 350° C. and then at 5° C./min up to 500° C., being kept at the temperature for 2 hours, to prepare a compound oxide of vanadium and zinc.

Catalyst 18

Vanadium (V) pentoxide produced by Katayama Kagaku was used as catalyst 18.

Evaluation of Catalysts

EXAMPLES 10 to 13

A glass three-neck flask was charged with 107.3 g of acetic anhydride, a predetermined amount of a catalyst (any of said catalysts 11 to 14) and 0.78 g of ammonium bromide, and the mixture was stirred at 500 rpm using stirring blades, while air was bubbled in at 50 ml/min at atmospheric pressure. In succession, the three-neck flask was heated in an oil bath, to be kept at 90° C., and 23.4 g of m-phenoxytoluene was added at a time from a dropping funnel, to start reaction. After completion of reaction for a predetermined time, the reaction solution was separated from the catalyst, and the reaction solution was analyzed by high performance liquid chromatography. The m-phenoxytoluene conversion, m-phenoxybenzyl acetate selectivity and m-phenoxybenzylidene diacetate selectivity were calculated from the following formulae:

m-phenoxytoluene conversion (%)=(Moles of reacted m-phenoxytoluene)/(Moles of m-phenoxytoluene in the raw materials)×100 m-phenoxybenzyl acetate selectivity (%)=(Moles of produced m-phenoxybenzyl acetate)/(Moles of reacted m-phenoxytoluene)×100 m-phenoxybenzylidene diacetate selectivity (%)=(Moles of produced m-phenoxybenzylidene diacetate)/(Moles of reacted m-phenoxytoluene)×100

The reaction conditions and results are shown in Tables 4 and 5.

Comparative Examples 4 and 5

Operation was effected as described for Example 10, except that said catalyst 16 or 17 was used as the catalyst. The reaction conditions and results are shown in Tables 4 and 5.

EXAMPLE 14

Operation was effected as described for Example 1, except that said catalyst 11 was used and that 16.08 g of m-chlorotoluene was used instead of 23.4 g of m-phenoxytoluene. The m-chlorotoluene conversion, m-chlorobenzyl acetate selectivity and m-chlorobenzylidene diacetate selectivity were calculated from the following formulae:

m-chlorotoluene conversion (%)=(Moles of reacted m-chlorotoluene)/(Moles of m-chlorotoluene in the raw materials)×100 m-chlorobenzyl acetate selectivity (%)=(Moles of produced m-chlorobenzyl acetate)/(Moles of reacted m-chlorotoluene)× 100 m-chlorobenzylidene diacetate selectivity (%)=(Moles of produced m-chlorobenzylidene diacetate)/(Moles of reacted m-chlorotoluene)×100

The reaction results are shown in Table 6.

EXAMPLE 15

A glass three-neck flask was charged with 107.3 9 of acetic anhydride, a predetermined amount of a catalyst (said catalyst 15), 0.88 g ot zinc (II) acetate dehydrate and 0.78 g of ammonium bromide, and the mixture was stirred at 500 rpm using stirring blades, while air was bubbled in at 50 ml/min at atmospheric pressure. In succession, the three-neck flask was heated in an oil bath, to be kept at 90° C., and 16.08 g of m-chlorotoluene was added at a time from a dropping funnel, to start reaction. After completion of reaction for a predetermined time, the reaction solution was separated from the catalyst, and the reaction solution was analyzed by high performance liquid chromatography. The reaction results are shown in Table 6.

Comparative Examples 6 and 7

Operation was effected as described for Example 15, except that said catalyst 16 or 18 was used as the catalyst. The reaction results are shown in Table 6.

TABLE 4

| | | | | Co-catalyst (g) | |
| --- | --- | --- | --- | --- | --- |
| | Reaction substrate *1 | Catalyst No. | Weight of catalyst (g) | Zn(CH$_3$COO)$_2$—2H$_2$O | NH$_4$Br |
| Example 10 | MPT | Catalyst 11 | 1.0 | — | 0.78 |
| Example 11 | MPT | Catalyst 12 | 1.0 | — | 0.78 |
| Example 12 | MPT | Catalyst 13 | 1.0 | — | 0.78 |
| Example 13 | MPT | Catalyst 14 | 1.0 | — | 0.78 |
| Example 14 | MCT | Catalyst 11 | 1.0 | — | 0.78 |
| Example 15 | MCT | Catalyst 15 | 0.34 | 0.88 | 0.78 |
| Comparative Example 4 | MPT | Catalyst 16 | 0.16 | — | 0.78 |
| Comparative Example 5 | MPT | Catalyst 17 | 1.0 | — | 0.78 |
| Comparative Example 6 | MCT | Catalyst 16 | 0.16 | 0.88 | 0.78 |
| Comparative Example 7 | MCT | Catalyst 18 | 0.36 | 0.88 | 0.78 |

*1: MPT = m-phenoxytoluene, MCT = m-chlorotoluene

TABLE 5

| | | | Reaction results *1 | | |
| --- | --- | --- | --- | --- | --- |
| | Reaction temperature (° C.) | Reaction time (h) | MPT conversion (%) | MPBACE selectivity (%) | MPBDACE selectivity (%) |
| Example 10 | 90 | 6 | 33.1 | 37.2 | 59.7 |
| Example 11 | 90 | 6 | 7.4 | 60.0 | 29.8 |
| Example 12 | 90 | 6 | 41.2 | 27.1 | 71.4 |
| Example 13 | 90 | 6 | 27.0 | 32.7 | 53.3 |
| Comparative Example 4 | 120 | 6 | 0.2 | 0 | 0 |
| Comparative Example 5 | 90 | 6 | 6.1 | 66.4 | 30.6 |

*1: MPT = m-phenoxytoluene, MPBACE = m-phenoxybenzyl acetate, MPBDACE = m-phenoxybenzylidene diacetate

TABLE 6

| | | | Reaction results *1 | | |
| --- | --- | --- | --- | --- | --- |
| | Reaction temperature (° C.) | Reaction time (h) | MPT conversion (%) | MPBACE selectivity (%) | MPBDACE selectivity (%) |
| Example 14 | 90 | 6 | 46.7 | 10.4 | 73.9 |
| Example 15 | 120 | 6 | 4.3 | 36.3 | 62.9 |
| Comparative Example 6 | 120 | 6 | 2.7 | 26.3 | 30.7 |
| Comparative Example 7 | 120 | 6 | 2.5 | 57.8 | 18.8 |

*1: MCT = m-chlorotoluene, MCBACE = m-chlorobenzyl acetate, MCBDACE = m-chlorobenzylidene diacetate From the above results, it can be seen that if a catalyst containing at least one selected from cobalt oxides, cerium oxides and manganese oxides is used as a catalyst for producing an alkyl group substituted aromatic compound diacyloxylated at the side chains, the acyloxylation reaction can take place efficiently.

EXAMPLE 16

A glass three-neck flask was charged with 107.3 g of acetic anhydride, 0.67 g of cerous (III) acetate monohydrate, 0.88 g of zinc (II) acetate dehydrate and 0.78 g of ammonium bromide, and the mixture was stirred at 500 rpm using stirring blades, while air was bubbled in at 50 ml/min at atmospheric pressure. In succession, the three-neck flask was heated in an oil bath, to be kept at 90°C., and 23.4 g of m-phenoxytoluene was added at a time from a dropping funnel, to start reaction. After completion of reaction for a predetermined time, the reaction solution was analyzed by high performance liquid chromatography. The m-phenoxytoluene conversion and m-phenoxybenzylidene diacetate selectivity were calculated from the following formulae:

m-phenoxytoluene conversion (%)=(Moles of reacted m-phenoxytoluene)/(Moles of m-phenoxytoluene in the raw materials)×100 m-phenoxybenzylidene diacetate selectivity (%)=(Moles of produced m-phenoxybenzylidene diacetate)/(Moles of reacted m-phenoxytoluene)×100

The reaction results are shown in Table 7.

Comparative Example 8

Operation was effected as described for Example 16, except that 0.50 g of cobalt acetate was further added. The reaction results are shown in Table 7.

EXAMPLE 17

Operation was effected as described for Example 16, except that 14.9 g of m-chlorotoluene was used as the reaction substrate instead of 23.4 g of m-phenoxytoluene, and that air was bubbled in at 150 ml/min. The m-chlorotoluene conversion and m-chlorobenzylidene diacetate selectivity were calculated from the following formulae:

m-chlorotoluene conversion (%)=(Moles of reacted m-chlorotoluene)/(Moles of m-chlorotoluene in the raw materials)×100 m-chlorobenzylidene diacetate selectivity (%)=(Moles of produced m-chlorobenzylidene diacetate)/(Moles of reacted m-chlorotoluene)×100

The reaction results are shown in Table 8.

Comparative Example 9

Operation was effected as described for Example 17, except that 0.50 g of cobalt acetate was further added. The reaction results are shown in Table 8.

Comparative Example 10

Operation was effected as described for Example 17, except that 0.49 g of manganese acetate was used instead of 0.67 g of cerium acetate. The reaction results are shown in Table 8.

EXAMPLE 18

A glass three-neck flask was charged with 51.9 g of acetic anhydride, 0.67 g of cerous (III) acetate monohydrate, 0.88 g of zinc (II) acetate dehydrate and 0.78 g of ammonium bromide, and the mixture was stirred at 500 rpm using stirring blades, while air was bubbled in at 150 ml/min at atmospheric pressure. In succession, the flask was heated in an oil bath, to be kept at 90° C., and 14.9 g of m-cyanotoluene was added at a time from a dropping funnel, to start reaction. After reaction for 10 hours, 0.1 g of ammonium bromide was added to the reaction system every hour 8 times. The m-cyanotoluene conversion and m-cyanobenzylidene diacetate selectivity were calculated from the following formulae:

m-cyanotoluene conversion (%)=(Moles of reacted m-cyanotoluene)/(Moles of m-cyanotoluene in the raw materials)×100
m-cyanobenzylidene diacetate selectivity (%)=(Moles of produced m-cyanobenzylidene diacetate)/(Moles of reacted m-cyanotoluene)×100

The reaction results are shown in Table 9.

TABLE 7

| | | | | Results of reaction *1 | |
|---|---|---|---|---|---|
| | Reaction substrate | Reaction temperature (° C.) | Reaction time (h) | MPT conversion (%) | MPBDACE selectivity (%) |
| Example 16 | MPT | 90 | 9 | 42.5 | 85.2 |
| Comparative Example 8 | MPT | 90 | 4 | 48.1 | 50.7 |

*1: MPT = m-phenoxytoluene, MPBDACE = m-phenoxybenzlidene diacetate

TABLE 8

| | | | | Results of reaction *1 | |
|---|---|---|---|---|---|
| | Reaction substrate | Reaction temperature (° C.) | Reaction time (h) | MCT conversion (%) | MCBDACE selectivity (%) |
| Example 17 | MCT | 90 | 11 | 50.7 | 87.1 |
| Comparative Example 9 | MCT | 90 | 3 | 50.5 | 58.1 |

TABLE 8-continued

|  | Reaction substrate | Reaction temperature (° C.) | Reaction time (h) | Results of reaction *1 | |
|---|---|---|---|---|---|
|  |  |  |  | MCT conversion (%) | MCBDACE selectivity (%) |
| Comparative Example 10 | MCT | 90 | 7 | 51.2 | 69.2 |

*2: MCT = m-chlorotoluene, MCBDACE = m = chlorobenzylidene diacetate

TABLE 9

|  | Reaction substrate | Reaction temperature (° C.) | Reaction time (h) | Results of reaction *1 | |
|---|---|---|---|---|---|
|  |  |  |  | MTN conversion (%) | MCNDACE selectivity (%) |
| Example 18 | MTN | 90 | 18 | 47.5 | 75.3 |

*3: MTN = m-tolunitrile, MCNDACE = m-cyanobenzylidene diacetate

From the above results, it can be seen that if a cerium compound is used as a catalyst in the absence of a cobalt compound and a manganese compound for producing an alkyl group substituted aromatic compound diacyloxylated at the side chains, the acyloxylation reaction can take place efficiently.

EXAMPLE 19

A glass three-neck flask was charged with 53.65 g of acetic anhydride, 0.67 g of cerous (III) acetate monohydrate, 0.88 g of zinc (II) acetate dehydrate and 0.73 g of magnesium (II) bromide, and the mixture was stirred at 500 rpm using stirring blades, while air was bubbled in at 150 ml/min at atmospheric pressure. In succession, the three-neck flask was heated in an oil bath, to be kept at 90° C., and 16.08 g of m-chlorotoluene was added at a time from a dropping funnel, to start reaction. After completion of reaction for a predetermined time, the reaction solution was analyzed by high performance liquid chromatography. The m-chlorotoluene conversion, m-chlorobenzyl acetate selectivity and m-chlorobenzylidene diacetate selectivity were calculated from the following formulae. The decomposition of acetic anhydride was expressed by the moles of acetic anhydride decomposed into acetic acid when 1 mole of m-chlorobenzylidene diacetate was produced (acetic anhydride decomposition rate).

m-chlorotoluene conversion (%)=(Moles of reacted m-chlorotoluene)/(Moles of m-chlorotoluene in the raw materials)×100 m-chlorobenzylidene diacetate selectivity (%)=(Moles of produced m-chlorobenzylidene diacetate)/(Moles of reacted m-chlorotoluene)×100

Acetic anhydride decomposition rate=[Moles of produced acetic acid)/2]/(Moles of produced m-chlorobenzylidene diacetate)

The reaction results are shown in Table 10.

EXAMPLE 20

Operation was effected as described for Example 19, except that 0.90 g of zinc bromide was used instead of 0.73 g of magnesium bromide.

The reaction results are shown in Table 10.

EXAMPLE 21

Operation was effected as described for Example 19, except that 3.10 g of bromine was used instead of 0.73 g of magnesium bromide. The reaction results are shown in Table 10.

EXAMPLE 22

Operation was effected as described for Example 19, except that 0.78 g of ammonium bromide was used instead of 0.73 g of magnesium bromide. The reaction results are shown in Table 10.

EXAMPLE 23

Operation was effected as described for Example 19, except that 1.16 g of magnesium bromide hexahydrate was used instead of 0.73 g of magnesium bromide. The reaction results are shown in Table 10.

TABLE 10

|  | Catalyst | | Substrate | Reaction time (h) | Conversion (%) | DACE compound selectivity *1 (%) | Acetic anhydride decomposition rate |
|---|---|---|---|---|---|---|---|
| Example 19 | Ce(OAc)$_3$H$_2$O<br>Zn(OAc)$_2$2H$_2$O<br>MgBr$_2$ | 0.67 g<br>0.88 g<br>0.73 g | m-chlorotoluene | 5 | 37.3 | 78.7 | 1.74 |
| Example 20 | Ce(OAc)$_3$H$_2$O<br>Zn(OAc)$_2$2H$_2$O<br>ZnBr$_2$ | 0.67 g<br>0.88 g<br>0.90 g | m-chlorotoluene | 7 | 41.8 | 77.2 | 1.52 |
| Example 21 | Ce(OAc)$_3$H$_2$O<br>Zn(OAc)$_2$2H$_2$O<br>Br$_2$ | 0.67 g<br>0.88 g<br>3.10 g | m-chlorotoluene | 9 | 33.1 | 76.8 | 1.99 |
| Example 22 | Ce(OAc)$_3$H$_2$O<br>Zn(OAc)$_2$2H$_2$O | 0.67 g<br>0.88 g | m-chlorotoluene | 8 | 39.4 | 75.8 | 2.11 |

TABLE 10-continued

|  | Catalyst | | Substrate | Reaction time (h) | Conversion (%) | DACE compound selectivity *1 (%) | Acetic anhydride decomposition rate |
|---|---|---|---|---|---|---|---|
| Example 23 | NH$_4$Br$_2$<br>Ce(OAc)$_3$H$_2$O<br>Zn(OAc)$_2$2H$_2$O<br>MgBr$_2$6H$_2$O | 0.78 g<br>0.67 g<br>0.88 g<br>1.16 g | m-chlorotoluene | 7 | 34.7 | 78.7 | 2.35 |

DACE compound:

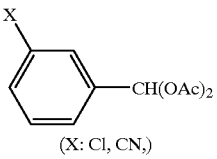

(X: Cl, CN,)

EXAMPLE 24

A glass three-neck flask was charged with 106.3 g of acetic anhydride, 0.67 g of cerous (III) acetate monohydrate, 0.88 g of zinc (II) acetate dehydrate and 0.73 g of magnesium (II) bromide, and the mixture was stirred at 500 rpm using stirring blades, while air was bubled in at 150 ml/min at atmospheric pressure. In succession, the three-neck flask was heated in an oil bath, to be kept at 90° C., and 14.9 g of m-cyanotoluene was added at a time from a dropping funnel, to initiate reaction. After completion of reaction for a determined time, the reaction solution was analyzed by high performance liquid chromatography. The m-cyanotoluene conversion, m-cyanobenzyl acetate selectivity and m-cyanobenzylidene diacetate selectivity were calculated from the following formulae. The decomposition of acetic acid was expressed by the moles of acetic anhydride decomposed into acetic acid when 1 mole of m-cyanobenzylidene diacetate was produced (acetic anhydride decomposition rate).

m-cyanotoluene conversion (%)=(Moles of reacted m-cyanotoluene)/(Moles of m-cyanotoluene in the raw materials)×100
m-cyanobenzylidene diacetate selectivity (%)=(Moles of produced m-cyanobenzylidene diacetate)/(Moles of reacted m-cyanotoluene)×100
Acetic anhydride decomposition rate=[(Moles of produced acetic acid)/2]/(Moles of produced m-cyanobenzylidene diacetate)

The reaction results are shown in Table 11.

EXAMPLE 25

Operation was effected as described for Example 24, except that 1.16 g of magnesium bromide hexahydrate was used instead of 0.73 g of magnesium bromide. The reaction results are shown in Table 11.

TABLE 11

|  | Catalyst | | Substrate | Reaction time (h) | Conversion (%) | DACE compound selectivity *1 (%) | Acetic anhydride decomposition rate |
|---|---|---|---|---|---|---|---|
| Example 24 | Ce(OAc)$_3$H$_2$O<br>Zn(OAc)$_2$2H$_2$O<br>MgBr$_2$ | 0.67 g<br>0.88 g<br>0.73 g | m-cyanotoluene | 8 | 22.5 | 90.7 | 1.48 |
| Example 25 | Ce(OAc)$_3$H$_2$O<br>Zn(OAc)$_2$2H$_2$O<br>MgBr$_2$6H$_2$O | 0.67 g<br>0.88 g<br>1.16 g | m-cyanotoluene | 8 | 25.3 | 89.5 | 2.26 |

DACE compound:

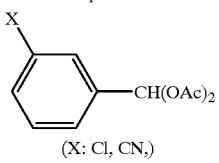

(X: Cl, CN,)

From the above results, it can be seen that if a solid catalyst in which at least one selected from cobalt, cerium and manganese is supported on a solid material or a catalyst containing at least one selected from cobalt oxides, cerium oxides and manganese oxides is used as a catalyst, or if a cerium compound is used as a catalyst in the absence of a cobalt compound and a manganese compound, while a halogen compound which is neither crystal water nor ammonium ion is used as a co-catalyst, for producing an alkyl group substituted aromatic compound diacyloxylated at the side chains, the acyloxylation reaction can take place efficiently, and the decomposition of the carboxylic anhydride can be inhibited.

EXAMPLE 26

A glass three-neck flask was charged with 53.65 g of acetic anhydride, 0.67 g of cerous (III) acetate monohydrate as a catalyst, 0.88 g of zinc (II) acetate dihydrate and 0.78 g of ammonium bromide, and the mixture was stirred at 500 rpm using stirring blades, while air was bubled in at 150 ml/min at atmospheric pressure. In succession, the three-neck flask was heated in an oil bath, to be kept at 90° C., and 16.08 g of m-chlorotoluene was added at a time from a dropping funnel, to start reaction. After initiation of reaction, 0.1 g of ammonium bromide was added every hour 8 times. The reaction solution was sampled at predetermined time intervals and analyzed by high performance liquid chromatography. The m-chlorotoluene conversion and m-chlorobenzylidene diacetate yield were calculated from the following formulae:

m-chlorotoluene conversion (%)=(Moles of reacted m-chlorotoluene)/(Moles of m-chlorotoluene in the raw materials)×100 m-chlorobenzylidene diacetate yield (%)=(Moles of produced m-chlorobenzylidene diacetate)/(Moles of m-chlorotoluene in the raw materials)×100

The reaction results are shown in Table 12.

EXAMPLE 27

Operation was effected as described for Example 26, except that magnesium bromide was added by 0.73 g in the beginning and added by 0.07 g every hour, instead of adding ammonium bromide by 0.78 g in the beginning and by 0.1 g every hour. The reaction results are shown in Table 12.

EXAMPLE 28

A glass three-neck flask was charged with 53.65 g of acetic anhydride, 0.67 g of cerous (III) acetate monohydrate as a catalyst, 0.88 g of zinc (II) acetate dihydrate and 0.73 g of magnesiumbromide, and the mixture was stirred at 500 rpm using stirring blades, while air was bubled in at 150 ml/min at atmospheric pressure. In succession, the three-neck flask was heated in an oil bath, to be kept at 90° C., and 16.08 g of m-chlorotoluene was added at a time from a dropping funnel, to start reaction. The reaction solution was sampled at predetermined time intervals and analyzed by high performance liquid chromatography. The reaction results are shown in Table 12.

EXAMPLE 29

A glass three-neck flask was charged with 53.65 g of acetic anhydride, 0.67 g of cerous (III) acetate monohydrate and 0.90 g of zinc (II) bromide, and the mixture was stirred at 500 rpm using stirring blades, while air was blown in at 150 ml/min at atmospheric pressure. In succession, the three-neck flask was heated in an oil bath, to be kept at 90° C., and 16.08 g of m-chlorotoluene was added at a time from a dropping funnel, to start reaction. Immediately after initiation of reaction, air was fed at a rate of 1 ml/min through a liquid reservoir containing bromine, and saturated bromine gas was continuously supplied into the reaction system. The reaction results are shown in Table 12.

EXAMPLE 30

Operation was effected as described for Example 28, except that 3.1 g of bromine was used instead of 0.73 g of magnesium bromide.

TABLE 12

|  | Catalyst |  | Substrate | Reaction time (h) | Conversion (%) | DACE compound yield *1 (%) |
|---|---|---|---|---|---|---|
| Example 26 | Ce(OAc)$_3$H$_2$O | 0.67 g | m-chlorotoluene | 3 | 22.1 | 17.4 |
|  | Zn(OAc)$_2$2H$_2$O | 0.88 g |  | 5 | 35.8 | 28.1 |
|  | NH$_4$Br$_2$ | 0.78 g |  | 7 | 50.0 | 36.1 |
|  | (Furthermore, 0.10 g of NH$_4$Br was added every hour 8 times.) |  |  | 9 | 57.6 | 42.9 |
| Example 27 | Ce(OAc)$_3$H$_2$O | 0.67 g | m-chlorotoluene | 3 | 27.8 | 22.5 |
|  | Zn(OAc)$_2$2H$_2$O | 0.88 g |  | 5 | 37.1 | 29.5 |
|  | MgBr$_2$ | 0.73 g |  | 7 | 46.7 | 38.3 |
|  | (Furthermore, 0.07 g of MgBr$_2$ was added every hour 8 times.) |  |  | 9 | 51.8 | 40.4 |
| Example 28 | Ce(OAc)$_3$H$_2$O | 0.67 g | m-chlorotoluene | 3 | 25.7 | 20.3 |
|  | Zn(OAc)$_2$2H$_2$O | 0.88 g |  | 5 | 30.3 | 24.6 |
|  | MgBr$_2$ | 0.73 g |  | 7 | 34.5 | 27.4 |
| Example 29 | Ce(OAc)$_3$H$_2$O | 0.67 g | m-chlorotoluene | 3 | 29.2 | .21.9 |
|  | ZnBr$_2$ | 0.90 g |  | 5 | 44.1 | 33.5 |
|  | Br$_2$ saturated air 1 ml/min |  |  | 7 | 53.0 | 38.9 |
|  |  |  |  | 9 | 58.9 | 43.2 |
| Example 30 | Ce(OAc)$_3$H$_2$O | 0.67 g | m-chlorotoluene | 3 | 18.3 | 14.8 |
|  | Zn(OAc)$_2$2H$_2$O | 0.88 g |  | 5 | 25.4 | 20.0 |
|  | Br$_2$ | 3.10 g |  | 7 | 29.6 | 22.9 |

DACE compound:

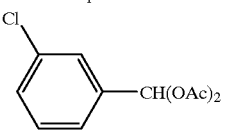

EXAMPLE 31

A glass three-neck flask was charged with 106.3 g of acetic anhydride, 0.67 g of cerous (III) acetate monohydrate, 0.88 g of zinc (II) acetate dehydrate and 0.78 g of ammonium bromide, and the mixture was stirred at 500 rpm using stirring blades, while air was bubled in at 150 ml/min at atmospheric pressure. In succession, the three-neck flask was heated in an oil back, to be kept at 90° C., and 14.9 g of m-cyanotoluene was added at a time from a dropping funnel, to start reaction. After initiation of reaction, 0.1 g of ammonium bromide was added every hour 8 times. The reaction solution was sampled at predetermined time intervals and analyzed by high performance liquid chromatography. The m-cyanotoluene conversion and m-cyanobenzylidene diacetate yield were calculated from the following formulae:

m-cyanotoluene conversion (%)=(Moles of reacted m-cyanotoluene)/(Moles of m-cyanotoluene in the raw materials)×100
m-cyanobenzylidene diacetate yield (%)=(Moles of produced m-cyanobenzylidene diacetate)/(Moles of m-cyanotoluene in the raw materials)×100

EXAMPLE 32

A glass three-neck flask was charged with 106.3 g of acetic anhydride, 0.67 g of cerous (III) acetate monohydrate as a catalyst, 0.88 g of zinc (II) acetate dehydrate and 0.78 g of ammonium bromide, and the mixture was stirred at 500 rpm using stirring blades, while air was bubled in at 150 ml/min at atmospheric pressure. In succession, the three-neck flask was heated in an oil bath, to be kept at 90° C., and 14.9 g of m-cyanotoluene was added at a time from a dropping funnel, to start reaction. The reaction solution was sampled at predetermined time intervals and analyzed by high performance liquid chromatography. The reaction results are shown in Table 13.

of H type β zeolite produced by PQ was supplied. The mixture was stirred for 20 hours, and the reaction solution was filtered, to separate the catalyst. To the mother liquor, 200 g of water and 100 g of ethyl acetate were added, and the oil phase was separated. Ethyl acetate was removed by evaporation, and to the residue, 100 g of n-hexane was added. The mixture was allowed to stand overnight at room temperature, to form a precipitate which was secured by filtration, sufficiently washed by n-hexane and dried in vacuum at 60° C. for 8 hours, to obtain m-chlorobenzylidene diacetate as crystal.

EXAMPLE 33

A three-neck flask was charged with 24.26 g of m-chlorobenzylidene diacetate and 6.15 g of sodium acetate, and the mixture was refluxed in a 200° C. oil bath for 9 hours. The mixture was cooled, and 100 g of ethyl acetate was added. Furthermore, saturated sodium hydrogencarbonate aqueous solution was added, and the mixture was sufficiently stirred, to produce m-chlorocinnamic acid which was extracted into a water phase. The water phase was separated, and hydrochloric acid was added till the pH became 2, to precipitate m-chlorocinnamic acid which was secured by filtration. It was washed by water sufficiently and dried in vacuum at 60° C. for 8 hours, being weighed. The purity of the obtained product was analyzed by high performance liquid chromatography. The m-chlorocinnamic acid yield and m-chlorobenzylidene diacetate conversion were obtained from the following formulae:

TABLE 13

| | Catalyst | | Substrate | Reaction time (h) | Conversion (%) | DACE compound yield *1 (%) |
|---|---|---|---|---|---|---|
| Example 31 | Ce(OAc)$_3$H$_2$O | 0.67 g | m-cyanotoluene | 3 | 20.4 | 18.0 |
| | Zn(OAc)$_2$2H$_2$O | 0.88 g | | 8 | 36.8 | 33.1 |
| | NH$_4$Br | 0.78 g | | | | |
| | (Furthermore, 0.10 g of NH$_4$Br was added every 1.5 hours 5 times.) | | | | | |
| Example 32 | Ce(OAc)$_3$H$_2$O | 0.67 g | m-cyanotoluene | 3 | 17.9 | 6.61 |
| | Zn(OAc)$_2$2H$_2$O | 0.88 g | | 5 | 24.7 | 22.2 |
| | NH$_4$Br | 0.78 g | | 8 | 29.3 | 25.9 |

DACE compound:

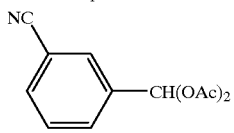

From the above results, it can be seen that in the method of using a solid catalyst in which at least one of cobalt, cerium and manganese is supported on a solid material or a catalyst containing at least one selected from cobalt oxides, cerium oxides and magnesium oxides, or using a cerium compound as a catalyst in the absence of a cobalt compound and a manganese compound, while using a halogen compound as a co-catalyst, for producing an alkyl group substituted aromatic compound diacyloxylated at the side chains, if said halogen compound is added continuously or intermittently to the reaction system, the acyloxylation reaction can take place efficiently.

Synthesis of m-chlorobenzylidene Diacetate

A three-neck flask was charged with 112.5 g of m-chlorobenzaldehyde and 163.2 g of acetic anhydride, and while the mixture was stirred in a 20° C. water bath, 3.5 g m-chlorocinnamic acid yield (%)=[(Weight of isolated m-chlorocinnamic acid)×(Purity)]/[(Molecular weight of m-chlorocinnamic acid)×(Moles of m-chlorobenzylidene diacetate supplied for reaction)]×100 m-chlorobenzylidene diacetate conversion (%)=(Moles of reacted m-chlorobenzylidene diacetate)/(Moles of m-chlorobenzylidene diacetate supplied for reaction)×100

The reaction results are shown in Table 14.

EXAMPLE 34

Operation was effected as described for Example 33, except that 7.36 g of potassium acetate was used instead of 6.15 g of sodium acetate. The reaction results are shown in Table 14.

EXAMPLE 35

Operation was effected as described for Example 33, except that 2.55 g of acetic anhydride was added further in addition to 24.26 g of m-chlorobenzylidene diacetate and 6.15 g of sodium acetate. The reaction results are shown in Table 14.

EXAMPLE 36

Operation was effected as described for Example 34, except that 5.30 g of sodium carbonate was used instead of 6.15 g of sodium acetate. The reaction results are shown in Table 14.

acid and/or a carboxylic anhydride can be caused to react with each other efficiently in the presence of an oxygen containing gas.

The alkyl group substituted aromatic compounds acyloxylated and diacyloxylated at the side chain obtained in the present invention are useful for perfumes, and the benzyl alcohols and benzaldehydes obtained by hydrolyzing them are useful for intermediate products of agricultural chemicals, drugs and perfumes and also for resin additives.

TABLE 14

|  | Supplied reacting species (molar ratio) | | | | MCDACE conversion (%) | MCCA yield (%) | MCCA purity (%) |
| --- | --- | --- | --- | --- | --- | --- | --- |
|  | MCDACE | $Ac_2O$ | AcONa | AcOK | $Na_2CO_3$ |  |  |  |
| Example 33 | 1 | — | 0.75 | — | — | 100 | 63.7 | 96.9 |
| Example 34 | 1 | — | — | 0.75 | — | 100 | 54.5 | 82.4 |
| Example 35 | 1 | 0.25 | 0.75 | — | — | 100 | 67.8 | 92.2 |
| Example 36 | 1 | — | — | — | 0.5 | 100 | 35.7 | 97.5 |

MCDACE = m-chlorobenzylidene diacetate, $Ac_2O$ = Acetic anhydride, MCCA = m-chlorocinnamic acid From the above results, it can be seen that if a benzylidene diacetate is heated in the presence of a basic catalyst, the corresponding cinnamic acid can be produced at a high yield.

Industrial Applicability

If (1) a solid catalyst in which at least one selected from cobalt, cerium and manganese is supported on a solid material or (2) a catalyst containing at least one selected from cobalt oxides, cerium oxides and manganese oxides is used, an alkyl group substituted aromatic compound and a carboxylic acid and/or a carboxylic anhydride can be caused to react with each other efficiently in the presence of an oxygen containing gas, and in addition the catalyst can be easily separated from the reaction solution.

(3) A compound diacyloxylated at the side chain can be highly selectively produced if a cerium compound is used as a catalyst in the absence of a cobalt compound and a manganese compound.

(4) If a halogen compound containing neither crystal water nor ammonium ion is used when a solid catalyst in which at least one selected from cobalt, cerium and manganese is supported on a solid material or a catalyst containing at least one selected from cobalt oxides, cerium oxides and manganese oxides is used as a catalyst, or when a cerium compound is used as a catalyst in the absence of a cobalt compound and a manganese compound, while said halogen compound is used as a co-catalyst, then an alkyl group substituted aromatic compound and a carboxylic anhydride can be caused to react with each other efficiently in the presence of an oxygen containing gas, and in addition, the decomposition of the carboxylic anhydride can be inhibited.

(5) If a halogen compound is supplied to the reaction system continuously or intermittently during reaction when a solid catalyst in which at least one selected from cobalt, cerium and manganese is supported on a solid material or a catalyst containing at least one selected from cobalt oxides, cerium oxides and manganese oxides is used as a catalyst, or when a cerium compound is used as a catalyst in the absence of a cobalt compound and a manganese compound, while said halogen compound is used as a co-catalyst, then an alkyl group substituted aromatic compound and a carboxylic acid and/or a carboxylic anhydride can be caused to react with each other efficiently in the presence of an oxygen containing gas.

Furthermore, as a new method for producing a cinnamic acid, if a benzylidene diacetate is used as a raw material, the corresponding cinnamic acid can be produced at a high yield. The cinnamic acids obtained by this method are useful for intermediate products of agricultural chemicals, drugs and perfumes.

What is claimed is:

1. A method for acyloxylating an alkyl group substituted aromatic compound at the side chain, by causing the alkyl group substituted aromatic compound and a carboxylic acid and/or a carboxylic anhydride to react with each other in the presence of an oxygen containing gas, wherein a solid catalyst is present in which at least one element selected from the group consisting of cobalt, cerium and manganese is supported on a solid supporting material.

2. A method for acyloxylating an alkyl group substituted aromatic compound at the side chain, by causing the alkyl group substituted aromatic compound and a carboxylic acid and/or a carboxylic anhydride to react with each other in the presence of an oxygen containing gas, wherein a catalyst is present comprising at least one oxide selected from the group consisting of cobalt oxide, cerium oxide and manganese oxide.

3. A method for acyloxylating an alkyl group substituted aromatic compound at a side chain, by causing the alkyl group substituted aromatic compound and a carboxylic acid and/or a carboxylic anhydride to react with each other in the presence of an oxygen containing gas, wherein a cerium compound is present as a catalyst in the absence of a cobalt compound and a manganese compound.

4. A method for acyloxlating an alkyl group substituted aromatic compound at the side chain, according to claim 3, wherein the cerium compound is soluble in the reaction solution.

5. A method for acyloxylating an alkyl group substituted aromatic compound at the side chain, according to any one of claims 1 through 4, where the alkyl group substituted aromatic compound is substituted at the meta position.

6. A method for acyloxylating an alkyl group substituted aromatic compound at the side chain, according to any one of claims 1–3, wherein the alkyl group substituted aromatic compound is a methyl group substituted aromatic compound.

7. A method for acyloxylating an alkyl group substituted aromatic compound at the side chain, according to any one of claims 1–3, wherein the carboxylic acid is an aliphatic carboxylic acid.

8. A method for acyloxylating an alkyl group substituted aromatic compound at the side chain, according to any one of claims 1–3, wherein the carboxylic anhydride is an aliphatic carboxylic anhydride.

9. A method for acyloxylating an alkyl group substituted aromatic compound at the side chain, according to any one of claims 1–3, wherein the reaction is effected in the presence of a halogen compound.

10. A method for acyloxylating an alkyl group substituted aromatic compound at the side chain, according to claim 9, wherein the halogen compound is a bromine compound.

11. A method for acyloxylating an alkyl group substituted aromatic compound at the side chain, according to claim 10, wherein the bromine compound either crystal water or ammonium ion.

12. A method for acyloxylating an alkyl group substituted aromatic compound at the side chain, according to claim 10, wherein the bromine compound is magnesium bromide or bromine.

13. A method for acyloxylating an alkyl group substituted aromatic compound at the side chain, according to claim 9, wherein the halogen compound is supplied continuously or intermittently to the reaction system during reaction.

14. A method for acyloxylating an alkyl group substituted aromatic compound at the side chain, according to any one of claims 1–3, wherein said reaction is effected in the presence of a zinc compound.

15. A method for acyloxylating an alkyl group substituted aromatic compound at the side chain, according to any one of claims 1–3, wherein the compound acyloxylated at the side chains is a compound diacyloxylated at the side chains.

16. A method for obtaining an aromatic aldehyde, comprising the step of hydrolyzing the alkyl group substituted aromatic compound diacyloxylated at the side chain obtained by the method stated in any one of claims 1–3, in the presence of water.

17. A method for producing a cinnamic acid, comprising the step of acyloxylating an alkyl group substituted aromatic compound at its side chain, by causing the alkyl group substituted aromatic compound to react with a carboxylic acid and/or a carboxylic anhydride in the presence of an oxygen containing gas and a solid catalyst in which at least one element selected from cobalt, cerium and manganese is supported on a solid material to form a benzylidene diacatate; and heating the resulting benzylidene diacetate in the presence of a basic catalyst.

18. A method for producing a cinnamic acid, according to claim 17, wherein said benzylidene diacetate is represented by the following general formula (1):

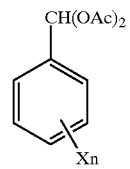

(1)

where X stands for at least one group selected from the group consisting of hydrogen atom, halogen group, alkoxy group, hydroxyl group, acyloxy group, nitro group, allyl group, alkyl group, aryl group, cyano group, amino group, amide group, acyl group, carboxyl group, formyl group and hydroxymethyl group, and n represents an integer from 1 to 5.

19. A method for producing a cinnamic acid, according to claim 17, wherein the basic catalyst is an alkali metal compound.

20. A method for producing a cinnamic acid, according to claim 19, wherein the alkali metal compound is a sodium compound or a potassium compound.

21. A method for producing a cinnamic acid, according to claim 17, wherein the benzylidene diacetate is heated at 100° C. or higher.

22. A method for producing a cinnamic acid, according to any one of claims 17 through 21, wherein acetic anhydride coexists in the reaction system when the cinnamic acid is produced from the benzylidene diacetate.

23. A method for producing a cinnamic acid, comprising the step of acyloxylating an alkyl group substituted aromatic compound at its side chain, by causing the alkyl group substituted aromatic compound to react with a carboxylic acid and/or a carboxylic anhydride in the presence of an oxygen containing gas and a solid catalyst selected from the group consisting of cobalt oxides, cerium oxides and manganese oxides and is supported on a solid material; and heating the resulting benzylidene diacetate in the presence of a basic catalyst.

24. A method for producing a cinnamic acid, comprising the step of acyloxylating an alkyl group substituted aromatic compound at its side chain, by causing the alkyl group substituted aromatic compound to react with a carboxylic acid and/or a carboxylic anhydride in the presence of an oxygen containing gas and a solid catalyst comprising a cerium compound in the absence of a cobalt compound and a manganese compound and is supported on a solid material; and heating the resulting benzylidene diacetate in the presence of a basic catalyst.

\* \* \* \* \*